United States Patent [19]

Gryaznov et al.

[11] 4,014,657
[45] Mar. 29, 1977

[54] CATALYTIC-REACTOR FOR CARRYING OUT CONJUGATE CHEMICAL REACTIONS

[76] Inventors: Vladimir Mikhailovich Gryaznov, Leninskie gory M.G.U. zona L, kv. 11; Viktor Sergeevich Smirnov, Kutuzovsky prospekt 26, kv. 555; Alexandr Petrovich Mischenko, Khersonskaya ulitsa 7, korpus 4, kv. 515; Sergei Ivanovich Aladyshev, ulitsa Grimau 7/2, korpus 4, kv. 77, all of Moscow, U.S.S.R.

[22] Filed: May 25, 1972

[21] Appl. No.: 256,935

[52] U.S. Cl. ............................. 23/288 R; 23/289; 23/252 R; 48/DIG. 5; 260/669 R; 260/683.3; 260/673.5; 55/16; 55/158

[51] Int. Cl.² .......................................... B01J 8/00

[58] Field of Search .............. 23/288 R, 289, 252; 48/DIG. 5; 260/669 R, 683.3, 673.5; 55/16, 158

[56] References Cited

UNITED STATES PATENTS

| | | |
|---|---|---|
| 3,241,293 | 3/1966 | Pfefferly ............................. 55/16 |
| 3,469,372 | 9/1969 | Yamauchi et al. ................. 55/158 |
| 3,534,531 | 10/1970 | Eguchi et al. ..................... 55/158 |
| 3,562,346 | 2/1971 | Smirnov et al. ................. 260/673.5 |

Primary Examiner—James H. Tayman, Jr.

[57] ABSTRACT

A catalytic reactor for carrying out conjugate chemical reactions, comprising a body with a system of plates arranged in said body parallel to one another and having their edges built into said body, said plates being made of a material selectively permeable to a reactant common to the reactions to be conjugated and possessing catalytic activity with regard to the both reactions being conjugated.

The said plates subdivide the inner space of the reactor body into a plurality of chambers intercommunicating in an alternate pattern through the intermediary of channels provided in the walls of the reactor body, so that two compartments are formed, each of these compartments serving for carrying out one of the two reactions being conjugated.

1 Claim, 2 Drawing Figures

CATALYTIC-REACTOR FOR CARRYING OUT CONJUGATE CHEMICAL REACTIONS

The present invention relates to chemical reactors and more particularly to catalytic reactors for carrying out conjugate chemical reactions without intermixing of the initial substances participating in the processes being conjugated. The reactor of the present invention may also find application for producing high-purity hydrogen from hydrocarbon stock materials.

A catalytic reactor for carrying out conjugate chemical reactions is known in the art, this reactor comprising a body with a partition accommodated therein. Said partition is constituted by a system of thin-walled tubes fixed on one side in the cover of the reactor and on the other side in the bottom thereof so that the reaction space of the apparatus is divided into two zones. The inner space of the reactor body serves for carrying out dehydrogenation reactions and the inner space of the tubes, for carrying out hydrodealkylation reactions. The tubes are made of a material selectively permeable to hydrogen and possessing catalytic activity in dehydrogenation and hydrodealkylation reactions.

With the reactor in operation, a hydrocarbon is fed into the tubes, this hydrocarbon undergoing dehydrogenation on the surface of the tube walls with evolution of hydrogen, while a hydrocarbon fed into the reactor outside of the tubes enters into the reaction of addition with hydrogen.

The hydrogen which evolves in the course of dehydrogenation inside the tube diffuses through the wall of the tube and enters on the external surface thereof into a reaction of addition with the hydrocarbon fed into the inner space of the reactor. Thus, conjugation of two reactions is ensured in the reactor without intermixing of the reactants, but only by virtue of the transfer of a reactant common to the both reactions, namely, of hydrogen, from one zone of the reactor into another.

The known reactor, however, is disadvantageous due to a small catalytically active surface area of the tubes per unit volume of the reactor. High throughput capacity of such reactor can therefore be ensured only by making the latter of a large volume, this being associated with the consumption of large quantities of costly materials.

Another disadvantage of the prior-art reactor of the type described resides in different dynamic conditions under which the processes are to take place in the intratubular and intertubular space of the reactor due to differences in the geometry of the external and internal surfaces of the tubes.

The last-mentioned disadvantage necessitates a very careful selection of dynamic conditions for carrying out the processes being conjugated, which makes the reactor operation more complicated.

It is an object of the present invention to provide such a catalytic reactor for carrying out conjugate chemical reactions, wherein the catalytically active surface area of the partition subdividing the reactor into two zones would be substantially larger per unit volume of the reactor than in the known reactor and wherein the same dynamic conditions would be ensured for carrying out coupled reactions in the both parts of the inner space of the reactor.

Said object is accomplished by providing a catalytic reactor for carrying out conjugate chemical reactions, comprising a body the inner space of which is divided by a partition into two compartments, each of these commpartments serving for carrying out one of the coupled reactions and being provided with pipes for feeding initial substances and for removing the reaction products, said partition being made of a material selectively permeable to a reactant common to the coupled reactions and possessing catalytic activity with regard to the both reactions being conjugated, according to the invention, partitions are made as a system of plates arranged parallel to one another and having edges built into the walls of the reactor body, thus dividing the inner space of the reactor into a plurality of chambers, said chambers intercommunicating in an alternate pattern through channels made in the walls of the reactor body.

The plates may be made corrugated.

Such a catalytic reactor, due to the possibility of arranging the plates thereof close to one another, allows an essential increase in the catalytically active surface area of the partition per unit volume of the reactor. The geometry of the both compartments of the present reactor is the same, whereby identical dynamic conditions are ensured for carrying out each of the reactions being conjugated. Another advantage offered by the present reactor is that it employs plates which are much easier to manufacture than tubular members, for example.

The present invention will become more fully apparent from a consideration of exemplary embodiments thereof described hereinbelow with due reference to the accompanying drawings, wherein.

Figure 1:
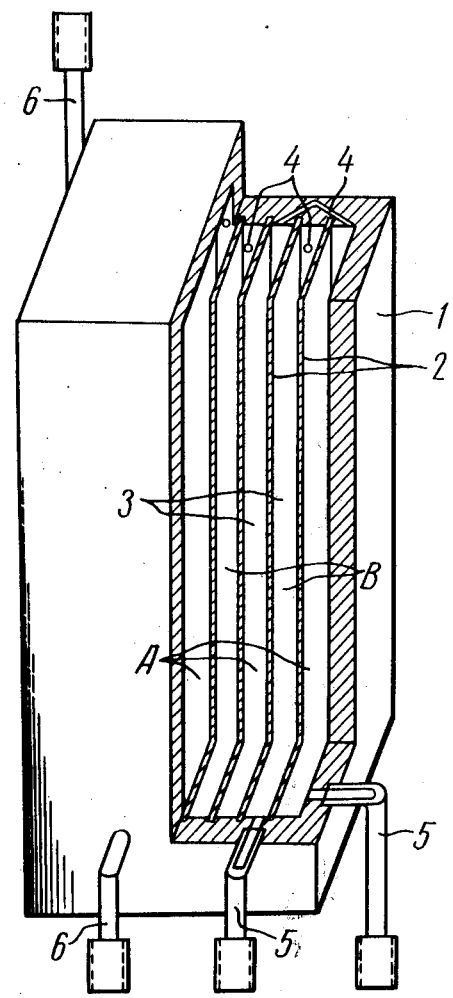
FIG. 1 shows a catalytic reactor for carrying out conjugate chemical reactions, according to the invention, partly in section.

Referring now to FIG. 1, the catalytic reactor of the invention for carrying out conjugate chemical reactions comprises a body 1, the inner space of which is subdivided into a plurality of chambers 3 by thin-walled plates 2 arranged parallel to one another and having edges built into the walls of the body 1. The plates 2 are made of a material selectively permeable to a reactant common to the reactions being conjugated and featuring catalytic activity with regard to the both reactions.

The chambers 3 are made to intercommunicate in an alternate pattern with the help of channels 4 provided in the walls of the body 1, Whereby the inner space of the body 1 is subdivided into two compartments A and B, each of these compartments having a pipe 5 for feeding an initial product and a pipe 6 for removing the reaction product.

Figure 2:
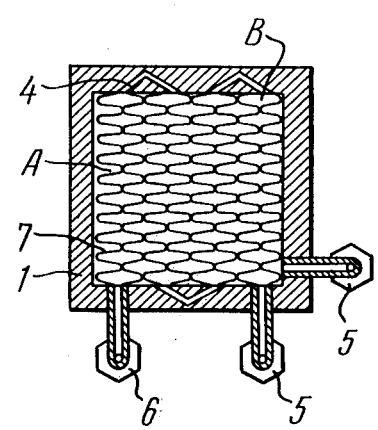
FIG. 2 is a cross sectionl view of a catalytic reactor for carrying out conjugate chemical reactions, according to the invention, with corrugated plates.

For precluding deformation of the the plates and for additionally increasing the active surface thereof, the latter may be made corrugated, as shown in FIG. 2 at 7. For enhancing the rigidity of the system of plates 7, it is preferable that the corrugations should be arranged in such a manner that convex portions of one plate 7 bear against the convex portions of the neighbouring plate 7.

The present catalytic reactor for carrying out conjugate chemical reactions operates as follows.

The reactor is heated to a temperature required for carrying out reactions to be conjugated. Through pipes 5 (FIG. 1) a substance required for carryiing out one of the conjugate reactions is fed into the compartment A, and a substance required for carrying out the other of the two reactions is fed into the compartment B. The first-mentioned substance starts reacting on the catalytically active surface of the plates 2 with the formation of the desired product and of a reactant common to the both conjugate reactions; this commonn reactant becomes dissolved in the material of the plates 2 and diffuses onto the opposite surface of the plates 2 into the compartment B wherein the second-mentioned substance is present. The common reactant having thus passed through the plate 2 starts reacting with the second substance, giving the second desired product. The resulting reaction products are removed from the compartments A and B through the pipes 6. It is possible to effect feeding of the first initial substance into the compartment B of the reactor, the second initial reactant being then fed into the compartment A thereof.

The present reactor can be employed for carrying out dehydrogenation, hydrogenation and hydrodealkylation reactions. In this case the thin-walled plates 2 are made from a palladium alloy, active, for example, for carrying out dehydrogenation and hydrodealkylation reactions. The compartment A is fed, for example, with isoamylene and the compartment B, with toluene.

Isoamylene enters into the dehydrogenation reaction with the formation of isoprene and evolution of hydrogen. This hydrogen is dissolved in the palladium alloy and diffuses onto the surface of the plates 2 that faces the compartment B. The highly active atomic hydrogen which has passed through the plates 2 reacts with toluene, the reaction products being benzene and methane.

The resulting isoprene and benzene are removed from the reactor through the pipes 6.

In the present reactor, due to the same structure of the chambers 3 which constitute the compartments A and B, the conditions required for carrying out conjugate reactions can be selected rapidly.

What is claimed is:

1. A catalytic reactor for carrying out conjugate chemical reactions, comrising a hollow body of rectangular cross-section covers for said body and a plurality of thin membranes within said body arranged parallel to one another and made of a material selectively permeable to hydrogen and having catalytic activity with respect to the conjugated reactions, said membranes being made in the form of plates whose edges are hermetically sealed into the body and covers of the reactor and which separate the reactor space into two groups of chambers interconnected in an alternate pattern by V-shaped channels formed in the side walls of the body, each group of said chambers having pipes for feeding in initial reactant and removing reaction products respectively and said plates being corrugated with a corrugation of one plate located opposite and bearing against the nearest corrugation of the adjacent plate.

* * * * *